United States Patent [19]
Powell et al.

[11] Patent Number: 5,462,524
[45] Date of Patent: Oct. 31, 1995

[54] METHODS FOR IMPROVING RECOVERY OF HEART FUNCTION FROM OPEN HEART SURGERY

[75] Inventors: Saul R. Powell, Woodmere; Anthony J. Tortolani, Manhasset, both of N.Y.

[73] Assignee: Research Corporation Technologies, Tuscon, Ariz.

[21] Appl. No.: 89,213

[22] Filed: Jul. 8, 1993

[51] Int. Cl.[6] .................................................. A61M 31/00
[52] U.S. Cl. ........................ 604/52; 424/614; 424/641; 128/898; 128/668
[58] Field of Search ............... 604/52, 53; 128/668–670, 128/898, DIG. 3; 424/569, 613–614, 641; 514/143

[56] References Cited

U.S. PATENT DOCUMENTS

| | | | |
|---|---|---|---|
| 4,416,280 | 11/1983 | Carpenter | 604/83 |
| 4,689,041 | 8/1987 | Corday et al. | 604/53 |
| 5,011,469 | 4/1991 | Buckberg et al. | 604/53 |
| 5,021,045 | 6/1991 | Buckberg et al. | 604/55 |
| 5,033,998 | 7/1991 | Corday et al. | 604/53 |
| 5,080,886 | 1/1992 | Mickle | 424/10 |
| 5,130,230 | 7/1992 | Segall et al. | 435/1 |
| 5,322,500 | 6/1994 | Johnson et al. | 604/56 |

OTHER PUBLICATIONS

Powell, et al., *The Effect of Zinc on Reperfusion Arrhythmias in the Isolated Perfused Rat Heart*, Free Radical Biology & Medicine, vol. 8, pp. 33–46, 1990.

Jurmann, et al., *Oxygen–derived free radical scavengers for amelioration of reperfusion damage in heart transplantation*, J. Thorac Cardiovasc Surg. 1988, 95:368–77.

Powell, et al., *Recent Advances in the Role of Reactive Oxygen Intermediates in Ischemic Injury*, Journal of Surgical Research, vol. 53, No. 4, 1992.

Chvapil, et al., *Effect of Zinc on Acute and Chronic Isoproterenol Induced Heart Injury*, Journal of Molecular and Cellular Cardiology, 1977, 9, 151–159.

Jeffrey, et al., *The Effect of Zinc on NADPH Oxidation and Monooxygenase Activity in Rat Hepatic Microsomes*, Molecular Pharmacology, 23:467–473.

Chvapil, et al., *Protective Effect of Zinc on Carbon Tetrachloride–Induced Liver Injury in Rats*, Experimental and Molecular Pathology 19, 186–197 (1973).

Korbashi, et al., *Zinc Protects Escherichia Coli against Copper–mediated Paraquat–induced Damage*, The Journal of Biological Chemistry, vol. 264, No. 15, 8479–8482, 1989.

Singal, et al. *Role of free radicals in catecholamine–induced cardiomyopathy*, Can. J. Physical Pharmacol, vol. 60, 1982.

Aiuto et al., "Addition of zinc enhances the effectiveness of St. Thomas No. 2 cardioplegic solution in an in vitro model of hypothermic cardiac arrest" (1993), *The Pharmacologist*, 35:Abs. 298.

Bray et al., "The physiologic role of zinc as an antioxidant" (1990), *Free Radic. Biol. Med.*, 8:281–291.

Chevion, "A site-specific mechanism for free radical induced biological damage: the essential role of redox–active transition metals" (1988), *Free Radic. Biol. Med.*, 5:27–37.

Chevion, "Protection against free radical–induced and transition metal–mediated damage: the use of pull and push mechanisms" (1991), *Free Radic. Res. Commun.*, 12–13:691–696.

(List continued on next page.)

*Primary Examiner*—C. Fred Rosenbaum
*Assistant Examiner*—Chalin Smith
*Attorney, Agent, or Firm*—Scully, Scott, Murphy & Presser

[57] ABSTRACT

The present invention is directed to methods and cardioplegic solutions for improving cardiac function and recovery of a mammal after surgical procedures which arrest the heart. In particular the present invention provides methods of improving recovery of a mammal after surgery involving cardiopulmonary bypass when the heart of the mammal is subjected to cardioplegia which include infusing the mammal's heart for a sufficient time at the onset of cardioplegia with a cardioplegic solution which contains an sufficient amount of a zinc-ligand conjugate.

23 Claims, 6 Drawing Sheets

OTHER PUBLICATIONS

Chevion et al., "Zinc–a redox–inactive metal provides a novel approach for protection against metal–mediated free radical induced injury: study of paraquat toxicity in *E. Coli.*" (1990), *Adv. Exp. Med. Biol.*, 264:217–222.

Hegenauer et al., "Improved function of reperfused rabbit kidney following administration of zinc histidine" (1991), *J. Trace Elem. Exptl. Med.*, 4:103–107.

Naito et al. "Zinc–carnosine chelate compound (Z–103) attenuates acute gastric mucosal injury by ischemia–reperfusion in rats", (1990), *Adv. Exp. Med. Biol.*, 264:411–414.

Powell et al. "Zinc improves postischemic recovery of the isolated rat heart", (1993), *The Pharmacologist,* 35:Abs. 299.

Powell et al., "Zinc improves postischemic functional recovery of the isolated rat heart", (1992), *FASEB J.,* 6:Abs. 1247.

Saltman et al., "Oxidative stress: a radical view", (1989), *Semin. Hematol.,* 26:249–256.

Tanigawa et al., "Antioxidative action of zinc–carnosine compound Z–103", (1990), *Adv. Exp. Med. Bbiol.,* 264:223–228.

Yoshikawa et al., "Effect of zinc–carnosine chelate compound (Z–103), a novel antioxidant, on acute gastric mucosal injury induced by ischemia–reperfusion in rats", (1992), *Free Radic. Res. Commun.,* 14:289–296.

5,462,524

METHODS FOR IMPROVING RECOVERY OF HEART FUNCTION FROM OPEN HEART SURGERY

This invention was made with United States government support under grant number HL45534 awarded by the National Institutes of Health. The United States government may have some rights in the invention.

FIELD OF THE INVENTION

The present invention provides methods for improving post-operative recovery from surgery requiring cardiopulmonary bypass by including zinc, appropriately complexed to a physiologically acceptable ligand, in a cardioplegic solution used during hypothermic arrest of the heart. For example, relative to known procedures the methods of the present invention can improve cardiac function, e.g. systolic pressure development, contractility, myocardial compliance and left ventricular relaxation, after surgery requiring cardiopulmonary bypass.

BACKGROUND OF THE INVENTION

Many heart conditions require surgical repair, for example severe coronary heart disease, aneurysms of the heart, aorta or vena cava, coarctations (narrowings) of the aorta, heart valve abnormalities, arrhythmias, cardiac tumors, cardiac or great vessel trauma, and the like, can all necessitate surgery where cardiopulmonary bypass is performed. In infants and children congenital heart problems such as septal defects, trilogy or tetralogy of Fallot, and the like can similarly require bypass surgery.

For example, about one-third of all deaths occurring in affluent American and Western European societies are due to coronary artery disease. Moreover, almost all elderly people have some impairment of coronary artery circulation. While nonsurgical procedures are employed for less severe cases of coronary artery disease, surgery requiring cardiopulmonary bypass, e.g. aortic-coronary bypass surgery, frequently becomes necessary in the more severe cases.

The decision to perform surgery involving cardiopulmonary bypass is not made lightly since such surgical procedures have an approximate 4% to 5% mortality rate. Moreover, of the patients surviving such surgery, at least 10% experience complications.

To minimize the damage to cardiac tissue during bypass surgery surgeons frequently maintain the heart at cold temperatures and perfuse the heart with cardioplegic solutions to stop the heart from beating. Such an arrested heart is amenable to surgical manipulation, requires less oxygen and survives longer than an intermittently beating heart. However, improved procedures are obviously needed to reduce the mortality and morbidity rates of surgical procedures requiring cardiopulmonary bypass.

The present invention provides methods of improving recovery after bypass surgical procedures which require hypothermic cardioplegic arrest of the heart. The present methods include providing a therapeutically effective amount of a zinc-ligand conjugate in a cardioplegic solution used for cardioplegic arrest. While standardized cardioplegic solutions are available, such solutions do not contain added zinc.

Zinc has been characterized as an anti-oxidant and is thought to inhibit the mixed-function oxidase system, to inhibit liver tissue injury caused by lipid peroxidation, and to ameliorate chronic isoproternol induced heart injury and catecholamine-induced cardiomyopathy (Jeffery, 1983 Molec. Pharm. 23: 4467–473; Chvapil et al. 1973, Exp. Molec. Path. 19: 186–196; Chvapil et al. 1977 J. Molec. Cell. Card. 9: 151–159; and Singal et al. 1982 Can. J. Physiol. Pharmacol. 60: 1390–1397). Moreover, at physiological temperatures zinc has been shown to prevent arrhythmias and to improve heart function when administered during or after experimentally induced ischemia in isolated rat hearts (Powell et al. 1990 Free Radical Biol. & Med. 8: 33–46; Powell et al. 1992 FASEB J. 6 (5 Part I) Abst. No. 1799).

In a surprising departure from these prior art teachings the present inventors have discovered that administration of a zinc-ligand conjugate with cold incubation at the onset of cardioplegia provides an unexpected improvement in heart recovery from surgery. For example, the present methods can improve post-cardioplegic systolic pressure development, post-cardioplegic contractility and post-cardioplegic left ventricular relaxation in patients subjected to surgery requiring cardiopulmonary bypass.

The prior art teaches that zinc transport into endothelial cells is a facilitated process which is inhibited at cold temperatures (Bobilya et al. 1992 J. Cell. Physiol. 151: 1–7). Accordingly, the skilled artisan would not be motivated to administer zinc to hypothermic tissues. However, the present inventors have discovered that hypothermic cardioplegic heart tissues exhibit improved recovery of function when exposed to only low dosages of zinc, particularly when the zinc is administered at the onset of cardioplegia.

SUMMARY OF THE INVENTION

The present invention is directed to a method of improving recovery of a mammal after surgery when the heart of the mammal is subjected to cardioplegia by infusion with a cardioplegic solution at a hypothermic temperature; wherein the improvement includes infusing the heart for a sufficient time during at least the onset of cardioplegia with a cardioplegic solution which contains a sufficient amount of a zinc-ligand conjugate to improve cardiac function and recovery after surgery. In one embodiment the present methods deliver an effective dosage amount of a zinc-ligand conjugate to myocardial tissues to improve cardiac function and recovery after surgery.

The present invention is further directed to methods of improving post-cardioplegic systolic pressure development, post-cardioplegic contractility or post-cardioplegic left ventricular relaxation in a heart of a mammal after surgery requiring cardioplegia. These methods include infusing the heart for a sufficient time during at least the onset of cardioplegia with a cardioplegic solution which contains a sufficient amount of a zinc-ligand conjugate to deliver an effective dosage amount of zinc to myocardial tissues to improve post-cardioplegic systolic pressure development, contractility or left ventricular relaxation after cardioplegia.

In another embodiment the present invention is directed to a freshly prepared cardioplegic solution having a sufficient amount of a zinc-ligand conjugate to deliver an effective dosage amount of the conjugate to improve cardiac function and recovery from surgery. For example, such an improvement in cardiac function includes an improvement in post-cardioplegic systolic pressure development, contractility or left ventricular relaxation, after hypothermic cardioplegia.

DETAILED DESCRIPTION OF THE INVENTION

Figure 1:
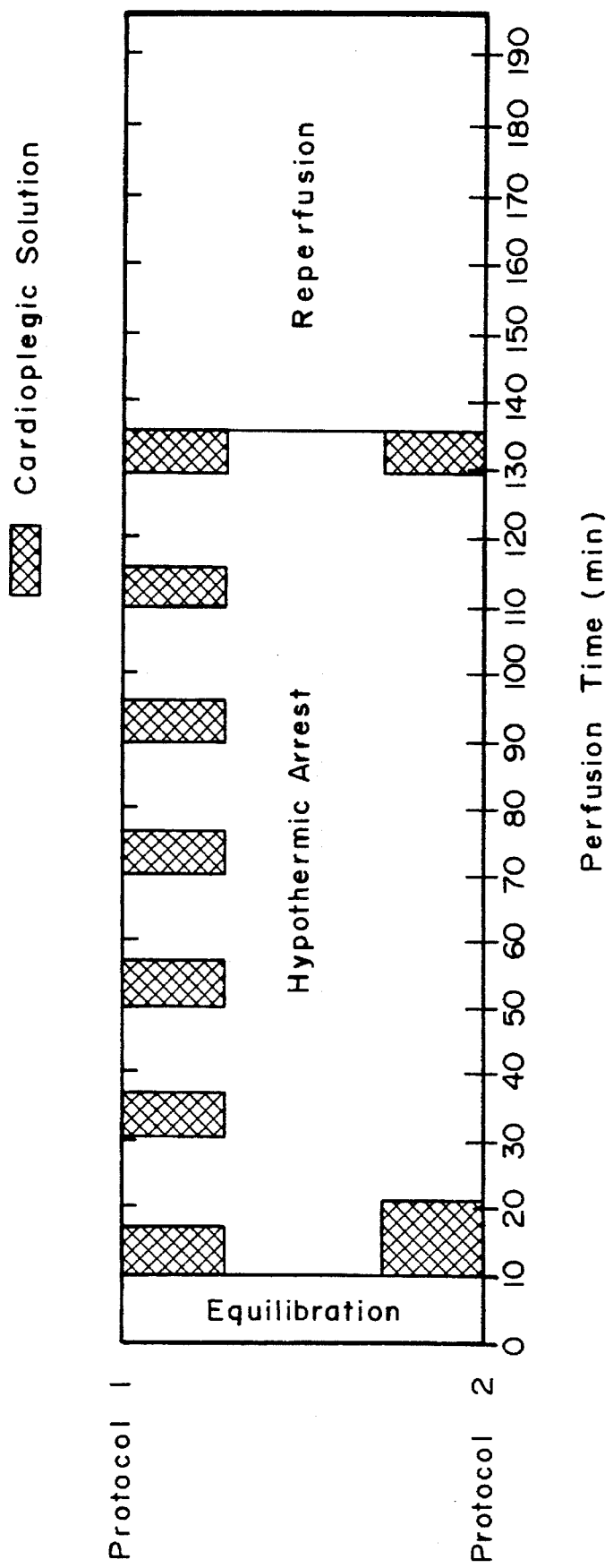
FIG. 1 summarizes experimental Protocols 1 (top) and 2 (bottom) utilized for perfusion of isolated rat hearts. Perfusion with cardioplegic solutions is depicted by hatching; when hearts are perfused with physiologic perfusion solutions there is no hatching. The times for each phase of the experiment, i.e. equilibration, hypothermic arrest and reperfusion, are also separately indicated.

The present invention relates to methods for improving the heart function and recovery from surgical procedures which necessitate cessation of heart activity, e.g. surgery requiring cardiopulmonary bypass. In particular, the present invention provides methods of improving recovery of a mammal after surgery involving cardiopulmonary bypass when the heart of the mammal is subjected to cardioplegia by infusion with a cardioplegic solution at a hypothermic temperature. The improvement provided by the present invention includes infusing the heart for a sufficient time during at least the onset of cardioplegia with a cardioplegic solution which contains a sufficient amount of a zinc-ligand conjugate to improve cardiac function and recovery of the mammal after surgery.

As used herein cardioplegia means that the heart beat is intentionally arrested by trained medical personnel, e.g. to permit surgical manipulation. During cardioplegia the blood supply to the heart is generally shunted around the heart and lungs and into peripheral tissues by a cardiopulmonary bypass system.

The present invention is directed to any surgical procedure involving cardioplegia. For example, the present invention can be utilized during surgical repair of severe coronary heart disease, aneurysms of the heart, aneurysms of the thoracic arteries, aneurysms of the thoracic veins, coarctations (narrowing) of the aorta, heart valve abnormalities or lesions, arrhyythmias, cardiac tumor, cardiac or great vessel trauma, and the like. Moreover the present methods can be used during implantation of pacemakers and during transplantation procedures.

The present invention can also be utilized to treat congenital heart problems in infants and children such as septal defects, anomalies of the pulmonary venous connection, valve lesions, trilogy or tetralogy of Fallot, single ventricle, malpositioning of the great arteries, congenital anomalies with the thoracic arteries and veins and the like.

Procedures for achieving cardioplegia are known to the skilled artisan, e.g. as described in Bojar (1992 Adult Cardiac Surgery Blackwell Scientific Publications, Cambridge, Mass.). While any known procedure for cardioplegia is contemplated, preferably such procedures include hypothermic cardioplegia, i.e. rapidly cooling the heart to temperatures of about 4° C. to about 12° C. as described in Bojar. A preferred hypothermic temperature is about 8° C.

Rapid cooling of the heart can arrest the heart, however such arrest may not be complete and hypothermic temperatures are utilized mainly to reduce the oxygen requirement of myocardial tissues. Moreover, when a heart does not receive blood, myocardial oxygen demand is determined primarily by the degree of electromechanical activity and secondarily by the temperature of the heart. Accordingly, surgeons generally utilize cardioplegic solutions to produce rapid and complete electromechanical diastolic arrest.

Rapid and complete arrest by cardioplegic solutions further preserves energy (ATP) stores, maintains energy-dependent cell membrane function, transmembrane electrolyte transport and provides energy for resumption of myocardial function. Oxygenated cardioplegic solutions can further provide oxygen to satisfy basal metabolic requirements and regenerate energy stores for repair of any preexisting or unintentionally induced cellular injuries. Moreover, fast and complete diastolic arrest by a cardioplegic solution can also protect myocardial tissues from injury caused by unexpected heart movement during surgery.

Immediate, i.e. fast and complete, diastolic arrest is generally accomplished by membrane depolarization using a cardioplegic solution containing potassium chloride at about 20 to about 25 millimolar (mM) concentrations. After diastolic arrest is achieved, lower secondary doses of about 8 to about 12 mM KCl can be utilized to maintain arrest.

Alternatively, magnesium can be used to achieve diastolic arrest at concentrations of about 30 millimolar to about 200 millimolar (Tyers 1982 Cardioplegic Additives—A Critical Review, in Engelman et al., eds. *A Textbook of Clinical Cardioplegia*, Futura Publishing Co. Inc., Mount Kisco, N.Y., pp. 139–156).

According to the present invention the subject conjugates of zinc are administered at the onset of cardioplegia. This means that the heart is exposed to the present zinc-containing conjugates within at least about 5 minutes of immediate diastolic arrest of the heart. In a preferred embodiment the subject zinc-containing conjugates, at the appropriate concentrations, are included in the cardioplegic solution used for immediate diastolic arrest of the heart. Accordingly the heart is preferably exposed to the present zinc-containing conjugates at the same time as the heart undergoes immediate diastolic arrest.

In addition to potassium chloride, cardioplegic solutions typically contain a buffer to prevent acidosis of myocardial tissues and calcium to maintain cell membrane integrity. A preferred pH for a cardioplegic solution at 17° C. is about 7.7 to about 8.0. More preferably the pH is maintained at approximately pH 8.0. The buffer used in a cardioplegic solution can, for example, be a Tris buffer or a bicarbonate buffer. Calcium is preferably added to a concentration of about 0.5 to about 1.5 mM, on the day of use.

Two general types of cardioplegic solutions are commonly used during open heart surgery, crystalloid and crystalloid:blood cardioplegic solutions. Either type is suitable for the present methods.

Crystalloid solutions do not contain blood and are composed of physiological salts and buffers. Such crystalloid solutions are available commercially, e.g. the St. Thomas No. 2 cardioplegic solution. As an alternative to obtaining such solutions from a commercial source, cardioplegic solutions can be made from known formulae which are readily available to the skilled artisan. For example, St. Thomas No. 2 cardioplegic solution contains 120 mM sodium, 16 mM potassium, 1.2 mM calcium, 16 mM magnesium, 160 mM chloride and 10 mM bicarbonate. St. Thomas No. 2 solution can be prepared as described in Braimbridge (1990 in Taylor K. M. ed. Cardiopulmonary Bypass. Principles and Management, Williams and Wilkins, Baltimore 375–389).

Crystalloid:blood cardioplegic solutions contain a mixture of blood and a crystalloid cardioplegic solution. The blood utilized is preferably the mammal's, e.g. the patient's, own blood. However, donor blood of the correct type can be used as a substitute or a supplement for the patient's blood. Preferably the blood utilized in the present cardioplegic solutions has a hematocrit of at least about 20%. Generally crystalloid:blood cardioplegic solutions contain about one part crystalloid solution and 4 parts blood, wherein the ionic concentrations of the crystalloid constituents are about fivefold higher to account for the dilution by blood. The hematocrit of the blood-based cardioplegic solution is preferably more than about 16%. Moreover, the overall concentration of potassium, calcium, magnesium, chloride and bicarbonate in crystalloid:blood cardioplegic solutions is more-or-less the same as in crystalloid cardioplegic solutions.

Preparation of blood:crystalloid cardioplegic solutions is known to the skilled artisan (Bojar 1992 *Adult Cardiac Surgery* Blackwell Scientific Publications, Cambridge, Mass.). For example, a modified UCLA blood-based cardioplegic solution includes a hematocrit of 18% to 22%, 22 mM potassium chloride, 0.5 mM calcium and a buffer to maintain the pH at about 7.9.

Both blood-based and non-blood-based cardioplegic solutions should have an osmolarity of about 330 to about 390 milliosmoles, i.e. somewhat hyperosmotic, to minimize the development of myocardial edema. Preferably the osmolarity is maintained at about 330 to about 350 milliosmoles. Solutions with an osmolarity exceeding 400 milliosmoles are preferably not employed. The desired osmolarity can be achieved by adding mannitol, glucose, colloid and the like to crystalloid solutions. Blood-based cardioplegic solutions tend to be slightly hyperosmolar and generally have good oncotic properties without any further additives.

All cardioplegic solutions should be sterile. Such sterile solutions can be prepared using sterile technique and sterile component stock solutions. Alternatively an assembled crystalloid cardioplegic solution can be sterilized after preparation, e.g. by filter or heat sterilization procedures. Heat sterilization should be performed only on crystalloid cardioplegic solutions to which calcium and the present zinc-containing conjugate have not yet been added. Calcium and the zinc-containing conjugate can be added after heat sterilization from freshly prepared, filter-sterilized stock solutions.

Prior to, and during administration, blood-based and non-blood-based cardioplegic solutions can be oxygenated by a bubble oxygenator, a membrane oxygenator, and the like. Oxygenated cardioplegic solutions provide oxygen to satisfy basal metabolic requirements and to regenerate energy stores for repair of cellular injury.

In one embodiment the present invention is directed to a freshly prepared cardioplegic solution having a sufficient amount of zinc, appropriately complexed to a physiologically acceptable ligand, to improve cardiac function and recovery of a mammal after hypothermic cardioplegia.

According to the present invention, any low molecular weight, physiologically acceptable ligand which binds zinc can be used to form the present zinc-ligand conjugates. As used herein a low molecular weight ligand has a molecular weight of less than about 500 g/mole. Such a ligand is generally anionic in character at the pH of the present cardioplegic solutions.

Moreover, while not wishing to limit the invention, any ligand which binds zinc with less affinity than the ligand binds copper is contemplated by the present invention. The binding constants of a ligand for zinc and copper can be readily ascertained by the skilled artisan. For example, Ashmead et al. (1985 *Intestinal Absorption of Metal Ions and Chelates* Charles C. Thomas, Publisher, Springfield, Ill.) provide methods determining such binding constants. Moreover, Ashmead et al. provide the binding constants of a variety of ligands which bind to zinc and other metal ions.

In one embodiment, ligands which can be conjugated with zinc and utilized to improve cardiac recovery after surgery include histidine (His), arginine (Arg), asparagine (Asn), lysine (Lys), proline (Pro), ethylenediamine, glycine (Gly), cysteine (Cys), aspartic acid (Asp), glutamic acid (Glu) and the like.

In a preferred embodiment, the zinc-ligand is a zinc-amino acid conjugate. Preferred amino acids for forming the present conjugates include His, Arg, Asn, Lys, Pro, Gly, Cys, Asp, Glu and the like. More preferred amino acids include His, Arg, Asn, Lys and Pro. The most preferred ligand or amino acid is His.

The conjugates contemplated herein provide zinc in a bidentate complex with the ligand. To prepare the present conjugates two molar equivalents of the ligand are added to the zinc cation and sufficient sodium bicarbonate is added to bring the pH to about 7.8. For example, a preferred zinc-ligand conjugate containing zinc and histidine, i.e. $Zn(His)_2$, can be prepared by adding two parts histidine to one part $ZnCl_2$ and then adjusting the pH to about 7.8.

Preferably the zinc-containing conjugate is freshly prepared and added to the cardioplegic solution on the day of use. Alternatively, zinc-containing conjugates can be stored as sterile lyophilized powders which are diluted with sterile water to the appropriate concentration and then added to the cardioplegic solution just prior to use.

According to the present invention, the concentration of a zinc-ligand conjugate in a cardioplegic solution is sufficient to improve cardiac function and recovery after surgery. Methods for assessing cardiac function during and after surgery are well-known to the skilled artisan and can be utilized to ascertain a preferred administered dosage of the present zinc-containing conjugates or to modulate the zinc conjugate dosage during surgery.

Several indicators are commonly measured to monitor cardiac function during and after surgery.

The structure of the recovering heart can be visualized after surgery using an echocardiography, angiography, radionuclide ventrilography, left ventriculography, and the like.

Cardiac output and other hemodynamic variables of the heart can be observed as a measure of cardiac function, e.g. cardiac index, systemic vascular resistance index, pulmonary vascular resistance index, means transmit time, central blood volume, stroke index, left ventricular stroke work, right ventricular stroke work, left cardiac work, and right cardiac work. Procedures for observing such variables are commonly available to the skilled artisan. For example, Guyton (1991 *Textbook of Medical Physiology*, eighth edition, W. B. Saunder Co., Philadelphia, Pa.) provides a description of methods for observing hemodynamic variables.

Moreover, the regularity and rate of the heart beat can be observed after surgery, e.g. from the pulse or an electrocardiogram. A regular heart beat is obviously desired; arrythmia is a sign of poor cardiac function and poor recovery from surgery. A normal heart rate is also desired; an injured heart may beat too slowly or race too quickly in an effort to supply sufficient blood to peripheral tissues.

Blood pressure, i.e. both diastolic and systolic pressures, is an important parameter measured for several reasons to assess heart function. For example, a low systolic pressure generally indicates that the stroke volume output is low and that the heart cannot contract properly. A small difference between systolic and diastolic pressures or a high diastolic pressure can indicate that the myocardial tissues may not be relaxing between heartbeats. A slow development of systolic pressure may indicate that a heart valve is closing poorly or that the heart is weakly or slowly contracting. A slow rate of fall of systolic function can also indicate that a valve is not closing properly or the heart is not contracting efficiently.

Moreover if the heart is not pumping blood efficiently, the blood can accumulate in the blood vessels of the lungs or of the peripheral tissues. Diminished cardiac output also diminishes the blood flow to the kidneys which can leads to retention of large quantities of fluids and disruption of the normal blood electrolyte balance. Fluid retention by the kidneys can progressively contribute to the blood volume and lead to life-threatening edema, especially acute pulmonary edema. After surgery or any potential trauma to the heart the skilled artisan is cognizant that the patient's physiological signs should be closely monitored for signs of edema, e.g. by observing urine output, blood electrolyte balance, blood volume, pulmonary function, and the like.

Therefore, a mammal's response to surgery and recovery therefrom can be assessed by numerous criteria, including the regularity and rate of the heart, the blood pressure, tissue fluid retention, urine output, the oxygenation and carbon dioxide levels of the blood, the blood electrolyte balance, the serum ammonia levels, the blood acid-base balance, the release of enzymes from damaged heart tissue, e.g. lactate dehydrogenase or creatine kinase, and the like. Normal values for these criteria and methods for measuring these criteria are commonly available (e.g. as in Bojar 1992 *Adult Cardiac Surgery* Blackwell Scientific Publications, Cambridge, Mass.; or Guyton 1991 *Textbook of Medical Physiology*, eighth edition, W. B. Saunder Co., Philadelphia, Pa.). Accordingly the skilled artisan can readily monitor the mammal and the mammal's heart and thereby ascertain the optimal response to a given dosage of the present zinc-ligand conjugates.

Specific dosage amounts can therefore be readily determined by one of ordinary skill in the art taking into account factors which can modify drug action, e.g. age, weight, sex, diet, disease state, times and methods of administration, and the like.

In general a sufficient amount of a zinc-ligand conjugate to improve cardiac function and recovery after hypothermic cardioplegia is a zinc-ligand conjugate concentration of about 5 micromolar to about 70 micromolar. A preferred concentration is about 10 micromolar to about 50 micromolar and an especially preferred concentration is about 30 micromolar to about 40 micromolar. In general, a volume of about 50 milliliters to about 10,000 milliliters of such a solution can be administered to the mammal.

In another embodiment the present invention is directed to a freshly prepared cardioplegic solution having a sufficient amount of a zinc-ligand conjugate to deliver an effective dosage amount of the zinc-ligand conjugate to improve cardiac function and recovery of a mammal after hypothermic cardioplegia.

In general, an effective dosage amount of the present zinc-containing conjugates is about 1.5 micromoles (μmoles) to about 150 μmoles as needed to attain beneficial therapeutic effects. A more preferred effective dosage amount is about 1.5 to about 75 μmoles. This amount can deliver about 0.01 mg to about 10 mg, and preferably about 0.1 to about 5 mg, of elemental zinc to myocardial tissues.

According to the present invention, zinc has optimal beneficial effects when administered during the onset of cardioplegia. However, depending upon the length of the surgery, the duration of cardioplegia, the needs of the patient and the individualized treatment procedures utilized by surgeons, the zinc-ligand conjugate can be administered throughout cardioplegia, up to a maximum dosage of about 150 micromoles of the zinc-containing conjugate or about 10 milligrams of elemental zinc. For example, about 5000 ml of a 30 μmolar zinc-ligand cardioplegic solution can be administered.

In one embodiment the time of zinc administration is at least about 10 minutes to about 3 hours. Preferably the time of zinc administration is at least about 10 minutes to about 35 minutes. The present zinc-ligand conjugates can be administered continuously or intermittently. For short surgical procedures, e.g. where cardioplegia occurs for less than about 10 to about 30 minutes, continuous zinc administration can be a method of choice. Alternatively, surgical procedures requiring cardioplegia for about 30 minutes or longer, can require intermittent administration of the cardioplegic/zinc solution to avoid excessive administration of zinc. Therefore, zinc can be administered intermittently by switching between cardioplegic solutions which do, and which do not, contain a zinc-conjugate. For example, about 10 µmoles to about 30 µmoles of the present conjugates can be administered for about 10 minutes approximately every 20 minutes for up to three hours. After each approximate 10 minute administration the zinc-containing cardioplegic solution can be replaced with a non-zinc-containing cardioplegic solution.

A dosage unit can further include other therapeutic agents beneficial for the recovery of a mammal from cardiac surgery. For example, some Kreb's cycle intermediates, e.g. glutamate and aspartate, can be added to stimulate oxidative metabolism and the production of ATP. Other therapeutic agents include free radical scavengers, e.g. mannitol, superoxide dismutase, peroxidase, catalase, allopurinol, alpha-tocopherol, ascorbic acid, deferoxamine and the like. Combinations of the present conjugates with such therapeutic agents can be administered either sequentially or simultaneously.

The present methods and cardioplegic solutions can be used in any mammal. However, such methods and solutions are preferably utilized for human patients.

Cardioplegic solutions containing the present zinc-containing conjugates can be administered by any known procedure. For example, a heart can be bathed with such solutions or the cardioplegic solution can be actively infused into the arterial or venous system of the heart. In general, active infusion of the heart provides faster and more complete arrest of the heart, a desirable benefit for myocardial preservation. Mechanical cardioplegic delivery systems are commercially available.

The following procedure is provided as a description of some of the events generally occurring during cardiac surgery and is not intended to limit the invention.

After the pericardium is incised and retracted, cardiopulmonary bypass and systemic cooling is initiated. The distal ascending aorta is then crossclamped and cold saline is poured over the heart to improve cardiac hypothermia. Cold crystalloid cardioplegic solution can be infused at a temperature of about 0° C. to about 5° C. Blood:crystalloid cardioplegic solution is generally infused when at about 4° C. to 10° C. Infusion is either antegrade into the aortic root or retrograde through the right atrium or the coronary sinus.

The decision to infuse the present zinc-containing cardioplegic solutions antegrade or retrograde is made with consideration for the mammal's condition. In general, antegrade infusion of cardioplegic solutions is preferred since such infusion is done through the natural coronary arterial system of the heart and the heart is arrested faster than when retrograde infusion is utilized. However retrograde infusion can be preferred when treating certain heart conditions. For example, retrograde infusion can be beneficial in patients with severe native vessel disease, during reoperations or when aortic insufficiency limits the efficacy of antegrade infusion. In patients with coronary artery disease, retrograde infusion can provide more uniform cooling distal to coronary obstructions. Antegrade infusion through the aortic root can also be problematical during aortic and mitral valve surgery and during aortic dissections.

The present cardioplegic solutions are preferably infused in an antegrade manner to attain an infusion pressure which is less than 150 mm Hg in the aortic root. More preferably the infusion pressure in the aortic root for crystalloid generally is about 20 mm Hg to about 60 mm Hg. Blood:crystalloid solutions are preferably infused at pressures of about 100 mm Hg.

Cardioplegic solutions are infused in a retrograde fashion through the right atrium at a rate of about 250 milliliters per minute at a pressure of less than about 60 millimeters Hg. When retrograde infusion is through the coronary sinus, cardioplegic solutions are infused at a rate of about 150 to 250 milliliters per minute and a pressure of no more than about 40 to about 60 millimeters Hg.

During cardioplegic infusion the myocardial temperature is monitored, e.g. with a thermistor placed at the left ventricular apex, and a temperature of less than 15° C. is maintained. Upon completion of the surgical manipulations of the heart, systemic cooling and the infusion of cardioplegic solution is terminated. The aorta can then be unclamped to reperfuse the heart with blood.

The heart can undergo injury during cardiopulmonary bypass, cardioplegia and the subsequent reperfusion of the heart with blood. For example, acute injuries include subendocardial necrosis, transmural necrosis, membrane peroxidation, membrane degeneration, intracellular edema, cell death, mitochondrial swelling and the like. Chronic injuries include ventricular dilation, myocardial fibrosis and the like.

These injuries can negatively impact the post-operative function of the heart. For example such injuries can lead to a slow or irregular heart beat, fibrillation, poor systolic pressure development, poor contractility, poor ventricular compliance, release of cellular proteases and enzymes, and the like.

The present invention can be used to prevent such injuries and improve cardiac function after cardioplegia. For example, when zinc is administered to cardioplegic hearts according to the methods of the present invention, the systolic pressure development post-cardioplegia was virtually identical to pre-cardioplegia pressure development. In contrast, hearts receiving cardioplegic solution without zinc had a post-cardioplegia systolic pressure development of only about 80% of the pre-cardioplegic value. Moreover, zinc-treated hearts had significantly better post-cardioplegic contractility, compliance and left ventricular relaxation than non-zinc-treated hearts.

Accordingly the present methods and cardioplegic solutions can also improve post-cardioplegic systolic pressure development, post-cardioplegic contractility and post-cardioplegic left ventricular relaxation in a heart of a mammal after surgery requiring cardioplegia. Such methods include infusing the heart for a sufficient time at the onset of cardioplegia with a cardioplegic solution which contains a sufficient amount of a zinc-ligand conjugate to deliver an effective dosage amount of zinc to myocardial tissues to improve post-cardioplegic systolic pressure development.

The following Examples further illustrate the invention.

EXAMPLE 1

Zinc Administration Improves Cardiac Function After Hypothermic Cardiac Arrest

MATERIALS AND METHODS

Animals

All studies were conducted in accordance with the "Guide for the Care and Use of Laboratory Animals" (NIH Publication No. 85-23, revised 1985) and were approved by the Institutional Animal Care and Use Committee of North Shore University Hospital. Male Sprague-Dawley rats (275–450 g) were obtained from Charles River Laboratory, Inc. (Wilmington, Mass.) or Taconic Farms (Germantown, N.Y.) and were allowed at least 3 days of in-house acclimatization before experimental use. During this time, all animals were allowed ad libitum access to Purina lab chow (Ralston Purina Co., St. Louis, Mo.) and water.

Chemicals and Reagents

Sodium bicarbonate, sodium chloride, potassium chloride, HEPES, magnesium sulfate, magnesium chloride, D-(+)-glucose, calcium chloride, zinc sulfate, and histidine were obtained from Sigma Chemical Company (St. Louis, Mo.). Sodium heparin and sodium pentobarbital were obtained from the North Shore University Hospital pharmacy. Therapeutic grade, 95% $O_2$/5% $CO_2$ was obtained from General Welding Supply Company (Westbury, N.Y.).

Perfused Heart Preparation

Rats were injected with sodium heparin (500 units, ip.) 30 minutes before being anesthetized with sodium pentobarbital (60 mg/kg, ip.). Hearts were removed rapidly and placed in ice-cold heparinized saline. The hearts were then orthogradely perfused through the coronary arteries at a constant pressure of 95 cm $H_2O$ as previously described in Powell et al. (1990 Free Radic. Biol. Med. 8: 33–46).

Perfusates

The perfusate solution was a modified Krebs-Henseleit buffer (NaCl 118 mM, KCl 6.1 mM, $CaCl_2$ 2.5 mM, $MgSO_4$ 1.2 mM, $NaHCO_3$ 25 mM, HEPES 1.0 mM and glucose 11.1 mM). Complete buffer was prepared the day of the experiment by mixing the proper amounts of concentrated stock solutions and adding the appropriate quantity of glucose and calcium chloride. All concentrated solutions, with the exception of magnesium sulfate, were treated with chelating resin beads (Chelex 100®, iminodiacetic acid, Sigma Chemical Co., St. Louis, Mo.).

St. Thomas No. 2 solution, i.e. Plegisol®, (Abbott Laboratories, Chicago; as described in Braimbridge (1990) in Taylor K. M. ed. Cardiopulmonary Bypass. Principles and Management, Williams and Wilkins, Baltimore 375–389) was used as a cardioplegic solution. The composition of this cardioplegic solution is provided in Table 1.

TABLE 1

COMPOSITION OF ST. THOMAS NO. 2 CARDIOPLEGIC SOLUTION

| Component | Concentration (mM) |
|---|---|
| Sodium | 120.0 |
| Potassium | 16.0 |
| Calcium | 1.2 |
| Magnesium | 16.0 |
| Chloride | 160.4 |
| Biocarbonate | 10.0 |

The cardioplegic solution was prepared as a 10-fold concentrated solution without calcium. On the day of the experiment, the cardioplegic concentrate was diluted and a proper amount of calcium added. A zinc-bis-histidial (Zn-$His_2$) complex (1 zinc:2 histidines) was prepared daily from freshly prepared 200X stock solutions of $ZnCl_2$ and histidine. Sufficient bicarbonate was added to bring the pH to 7.4. The requisite amount of the Zn-$His_2$ solution was then added to the cardioplegic solution.

Experimental Protocols

Two protocols were utilized to test when zinc can optimally be administered. Protocol 1 provided intermittent zinc administration in cardioplegic solution as depicted in FIG. 1. Isolated hearts were equilibrated with Krebs-Henseleit buffer at 37° C. for 10 minutes. During the two hours of hypothermic arrest, cardioplegic solution was reinfused for 5 minutes every 15 minutes. Test hearts received 30μM zinc in the cardioplegic solution; control hearts received cardioplegic solution without zinc. After the 2 hour hypothermic arrest, hearts were reperfused with Krebs-Henseleit buffer at 37° C. for 10 minutes.

Protocol 2 provided zinc only at the beginning and end of hypothermic arrest (FIG. 1). Isolated hearts were equilibrated with Krebs-Henseleit buffer at 37° C. for 10 minutes. Cardiac arrest was initiated with 10 minutes of perfusion with cardioplegic solution at 10° C. Test hearts received 40μM zinc in the cardioplegic solution; control hearts received cardioplegic solution without zinc. During arrest, no further cardioplegic solution was infused. However, just prior to reperfusion, hearts were perfused with hypothermic cardioplegic solution. Hearts were then reperfused for 60 minutes with Krebs-Henseleit buffer at 37° C.

During arrest cardiac temperature was maintained at 10° C. by immersion in cardioplegic solution contained in a thermostatically controlled, water-jacketed heart chamber.

Indices of Cardiac Function

Six indicators were measured to assess cardiac function during these experiments. Coronary flow was determined by a timed collection of coronary effluent. Heart rate was calculated from the R to R peak interval of the electrocardiogram. Left ventricular systolic pressure development and end diastolic pressure were determined by insertion of a latex balloon (0.1 ml) into the left ventricle as previously described (Powell et al. 1990). The balloon was connected to a pressure transducer which in turn was connected to a multi-channel polygraph (Hewlitt-Packard). The balloon was expanded to exert a physiologic end diastolic pressure of 5 mm Hg. Systolic pressure developed, or pulse pressure was calculated as the peak systolic pressure minus the end diastolic pressure. Contractility was calculated as the maximum rate of rise of the pressure curve, or $+dP/dt_{max}$, and the maximum isovolumetric rate of relaxation was calculated from the rate of fall of the pressure curve, or $-dP/dt_{max}$.

Exclusion Criteria

Hearts were excluded from the study if they failed to maintain a developed systolic pressure of at least 70 mm Hg, or a heart rate of at least 220 beats per minute during the 10 minute pretreatment equilibration period. Further, hearts were excluded if a persistent arrhythmia was present during the equilibration period.

Chemical Analysis

Lactic dehydrogenase activity in pulmonary artery effluent was expressed in Racker units and determined using the method described by Bergmeyer et al. (1963 in *Methods of Enzymatic Analysis*, Academic Press, London; 736–743).

Statistical Analysis

Analysis of differences of cardiac functional recovery and lactic dehydrogenase release were analyzed with a repeated measure analysis of variance (RMANOVA) in which the within factor was time. Differences between two individual groups were analyzed with an independent Student t-test. In all cases, results were considered to significant at the $P<0.05$ level. All statistics were performed with the SPSS/PC+ (SPSS Inc., Chicago) statistical analysis package.

RESULTS

Zinc Effects on Heart Rate

Figure 2A:
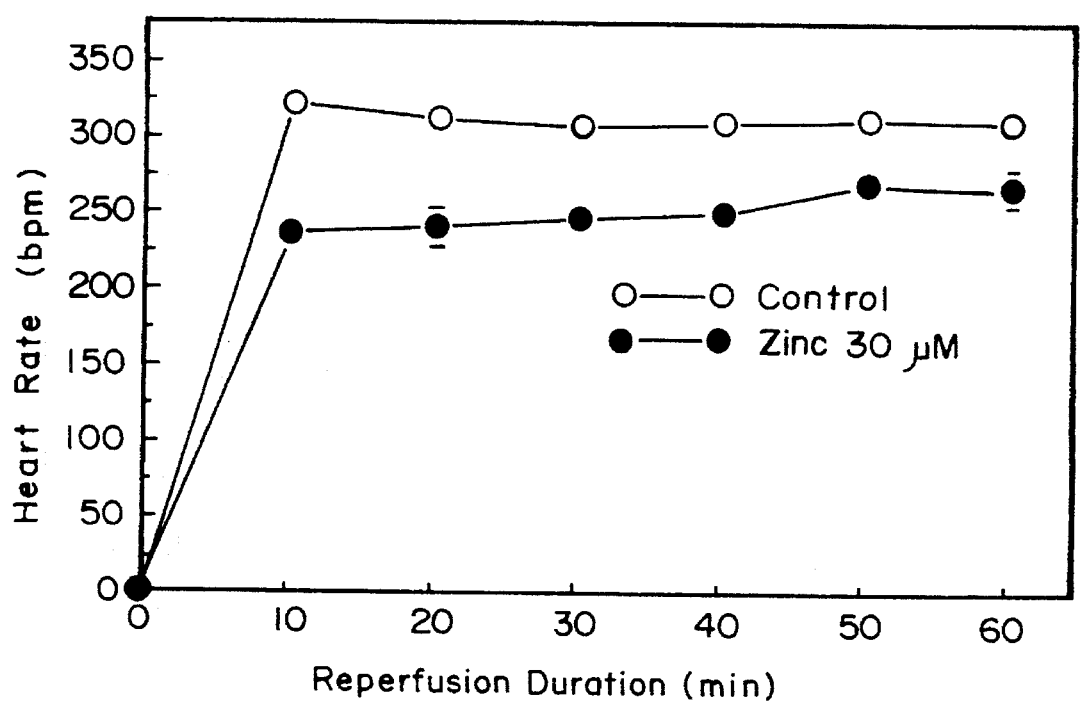
FIG. 2A depicts the heart rate of isolated rat hearts during reperfusion after hypothermic cardioplegic arrest according to Protocol 1. Open circle=Control hearts receiving no zinc. Closed circle=Test hearts receiving 30 μM zinc in the cardioplegic solution.
Figure 2B:
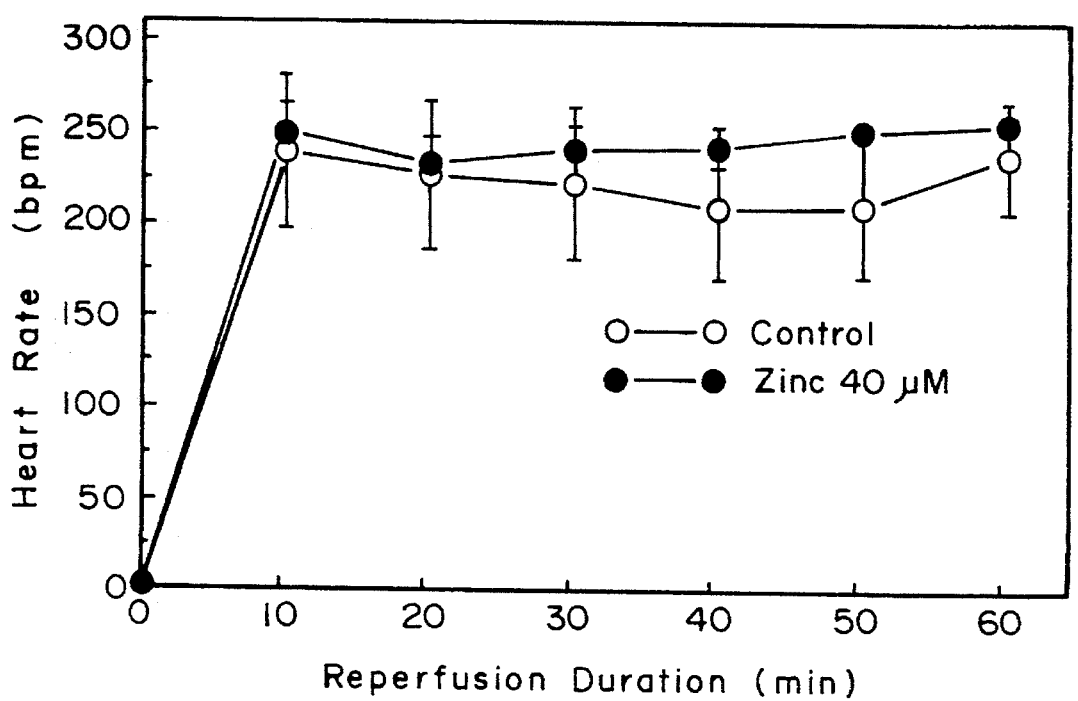
FIG. 2B depicts the heart rate of isolated rat hearts during reperfusion after hypothermic cardioplegic arrest according to Protocol 2. Open circle=Control hearts receiving no zinc. Closed circle=Test hearts receiving 40 μM zinc in the cardioplegic solution.

The effect of zinc-supplemented cardioplegic solutions on heart rate is illustrated in FIG. 2. Treatment of hearts with zinc according to Protocol 1, resulted in a significantly ($P<0.05$, RMANOVA) lower heart rate in the postcardioplegic period. By the end of the reperfusion period, heart rate in control versus zinc-treated hearts had returned to 95% and 80% of precardioplegic values, respectively. This was not the case for Protocol 2, as there were no significant differences between control and treated hearts. Heart rate, in both groups, had returned to approximately 80% of precardioplegic values by the end of the experiment.

Zinc Effects on Left Ventricular Systolic Pressure Development

Figure 3A:
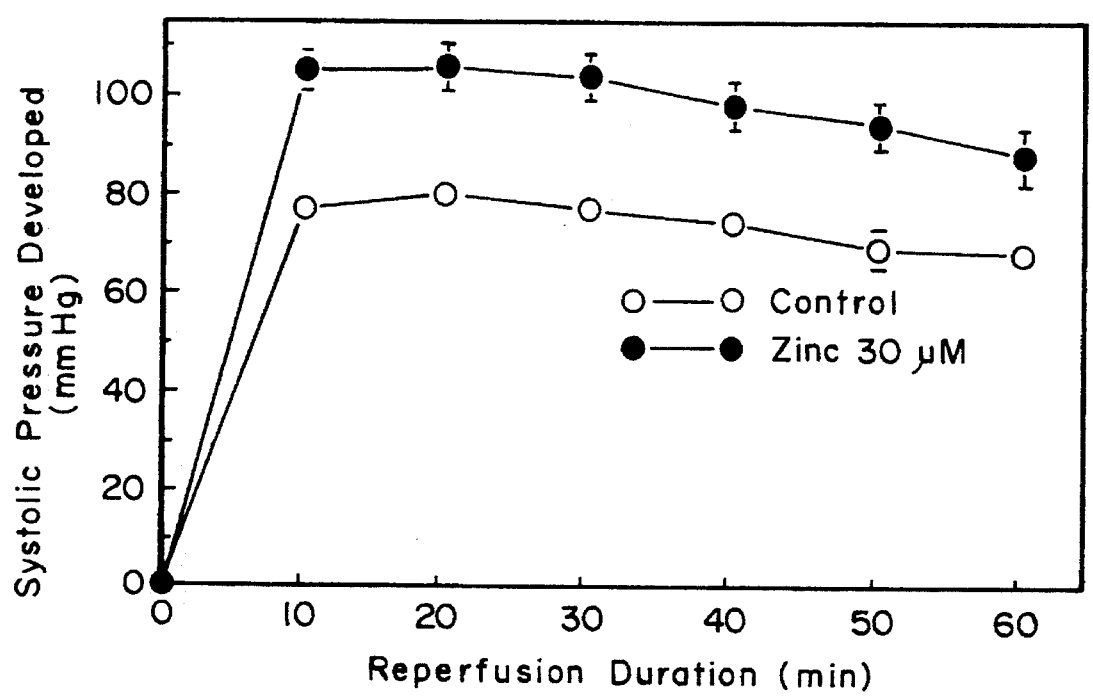
FIG. 3A depicts the left ventricular systolic pressure (in mm Hg) of isolated rat hearts during reperfusion after hypothermic cardioplegic arrest according to Protocol 1. Open circle=Control hearts receiving no zinc. Closed circle=Test hearts receiving 30 μM zinc in the cardioplegic solution.
Figure 3B:
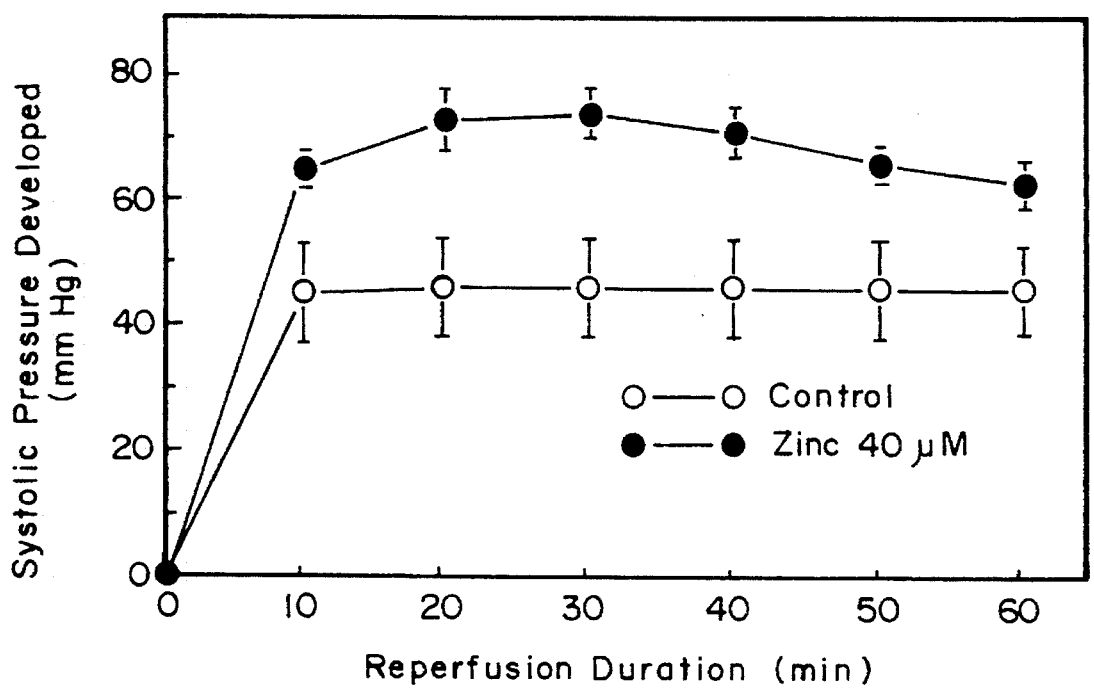
FIG. 3B depicts the left ventricular systolic pressure (in mm Hg) of isolated rat hearts during reperfusion after hypothermic cardioplegic arrest according to Protocol 2. Open circle=Control hearts receiving no zinc. Closed circle=Test hearts receiving 40 μM zinc in the cardioplegic solution.

The effect of zinc-supplemented cardioplegic solutions on systolic pressure development is illustrated in FIG. 3. Treatment of hearts with zinc according to both Protocols 1 and 2 resulted in significant ($P<0.05$, RMANOVA, for both protocols) improvement in postcardioplegic left ventricular systolic pressure development.

In particular, maximal recovery for zinc-treated hearts was virtually 100%, while that of control hearts was 80%, of precardioplegic values for hearts treated by Protocol 1. For hearts treated according to Protocol 2, maximal recovery was 76% for zinc-treated hearts but only 50% for non-zinc-treated control hearts.

Effect on Left Ventricular Contractility and Rate of Relaxation

Figure 4A:
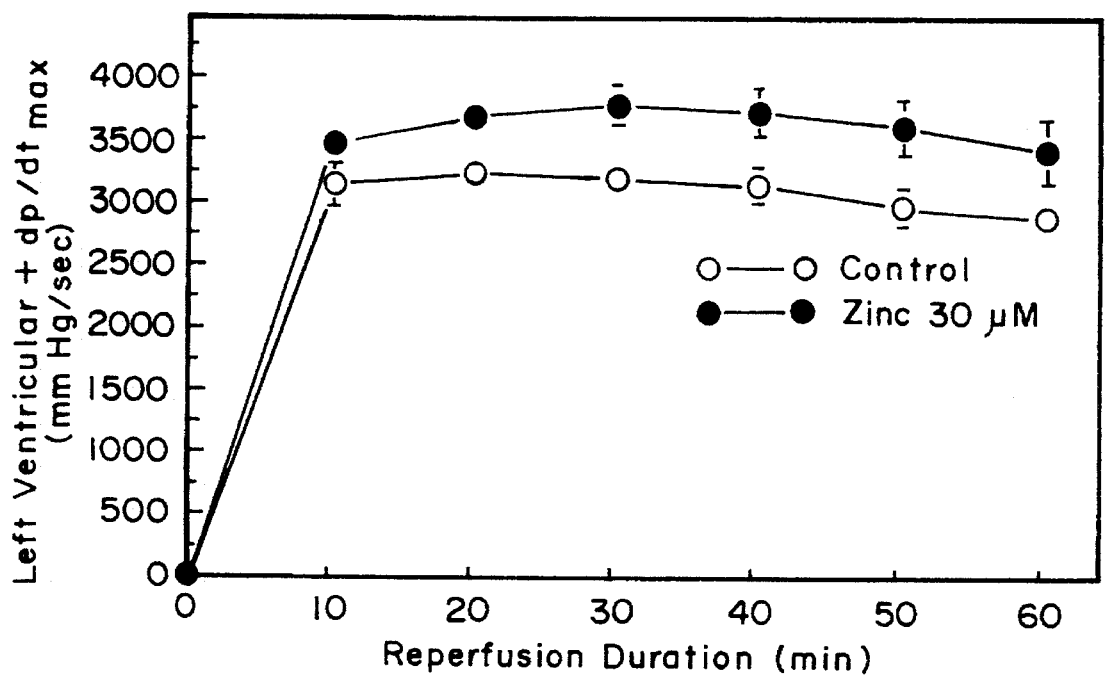
FIG. 4A depicts the left ventricular contractility (+dP/$dt_{max}$) of isolated rat hearts during reperfusion after hypothermic cardioplegic arrest according to Protocol 1. Open circle=Control hearts receiving no zinc. Closed circle=Test hearts receiving 30 μM zinc in the cardioplegic solution.
Figure 4B:
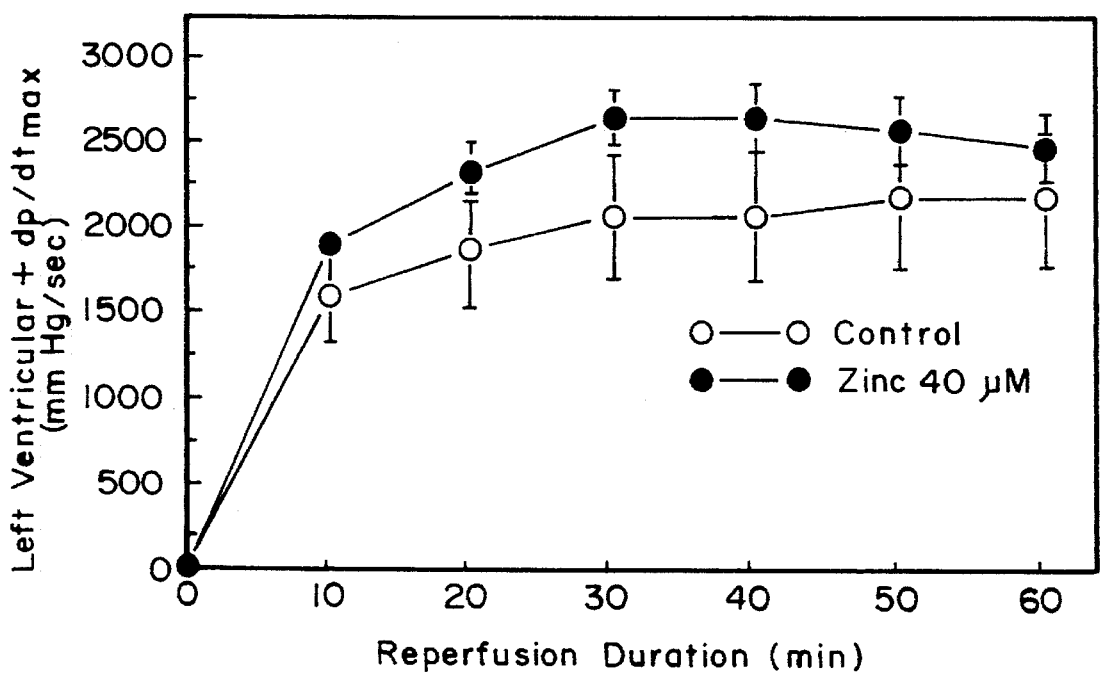
FIG. 4B depicts the left ventricular contractility (+dP/$dt_{max}$) of isolated rat hearts during reperfusion after hypothermic cardioplegic arrest according to Protocol 2. Open circle=Control hearts receiving no zinc. Closed circle=Test hearts receiving 40 μM zinc in the cardioplegic solution.

As illustrated in FIG. 4, contractility ($+dP/dt_{max}$) was improved in hearts treated with zinc. The improvement observed for hearts treated with zinc according to Protocol 1 was particularly significant ($P<0.05$, RMANOVA).

While the improvement in contractility for hearts treated with zinc according to Protocol 2 was apparent. However, a relatively large variability in contractility was observed for Protocol 2 control hearts, and this variability obscured the statistical significance of the zinc effect.

Figure 5A:
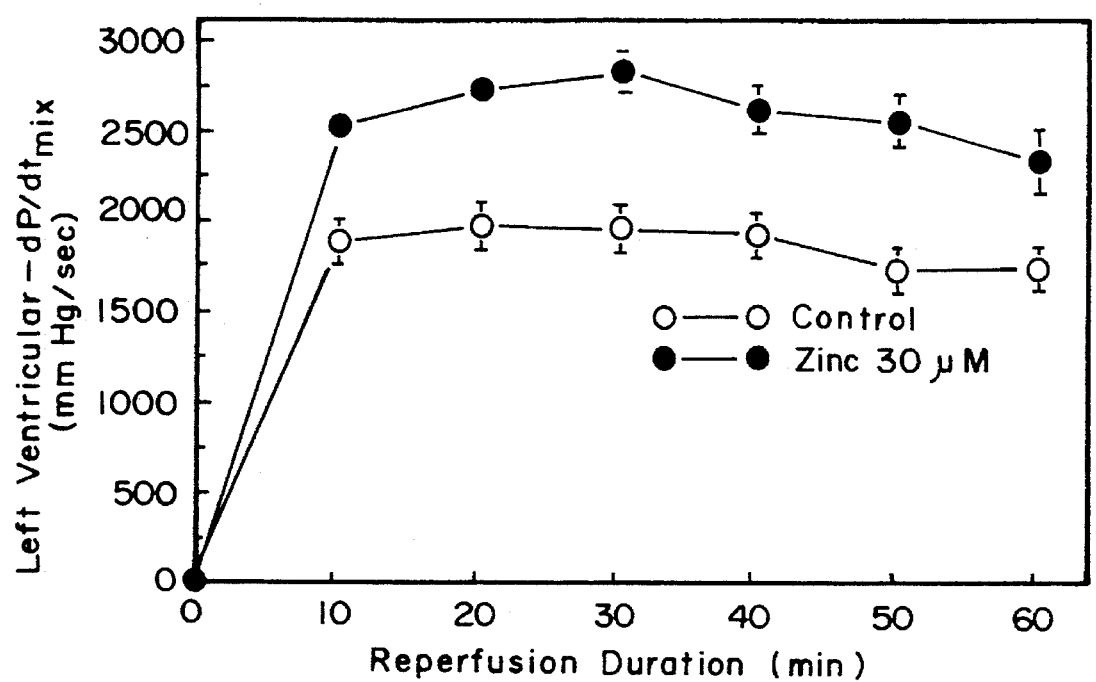
FIG. 5A depicts the left ventricular rate of relaxation (−dP/$dt_{max}$) of isolated rat hearts during reperfusion after hypothermic cardioplegic arrest according to Protocol 1. Open circle=Control hearts receiving no zinc. Closed circle=Test hearts receiving 30 μM zinc in the cardioplegic solution.
Figure 5B:
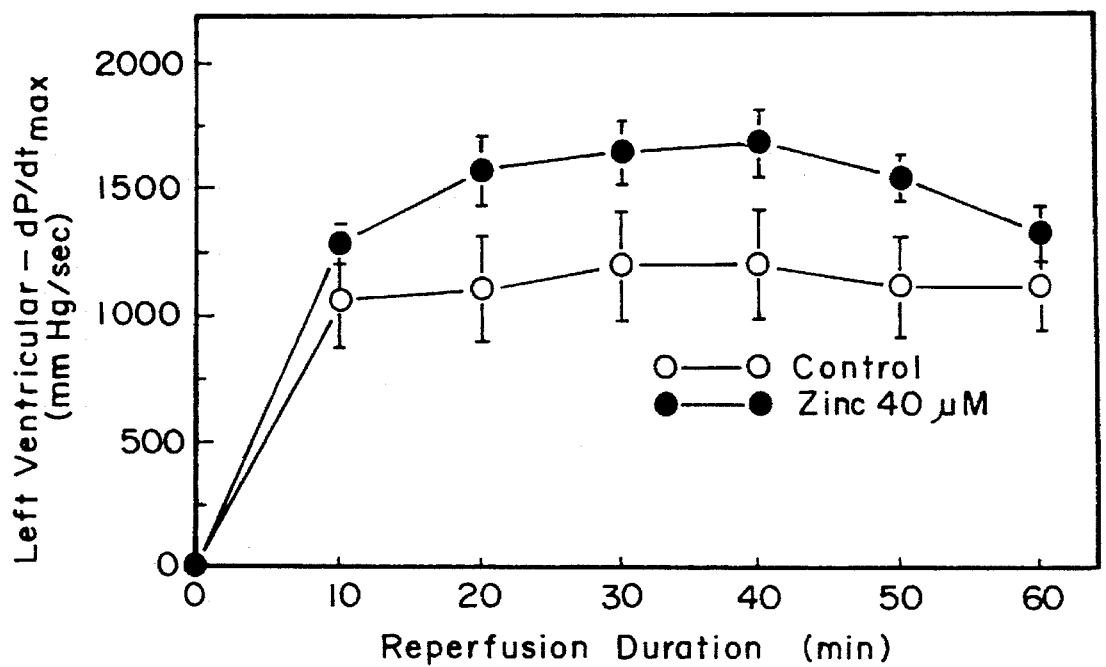
FIG. 5B depicts the left ventricular rate of relaxation (−dP/$dt_{max}$) of isolated rat hearts during reperfusion after hypothermic cardioplegic arrest according to Protocol 2. Open circle=Control hearts receiving no zinc. Closed circle=Test hearts receiving 40 μM zinc in the cardioplegic solution.

More marked improvements on the rate of left ventricular relaxation ($-dP/dt_{max}$) were observed in zinc-treatead hearts (FIG. 5). Differences between control and zinc-treated hearts were significant ($P<0.05$, RMANOVA) in both Protocol groups.

Effects on Lactate Dehydrogenase (LDH) Release

Figure 6A:
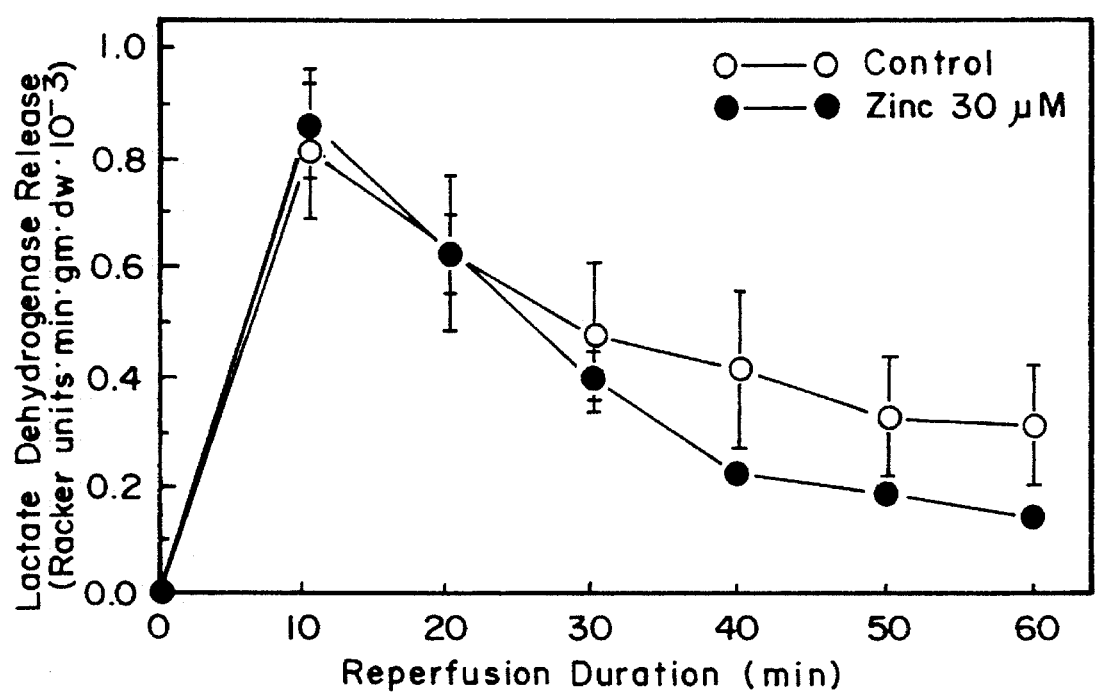
FIG. 6A depicts the amount of lactate dehydrogenase released from isolated rat hearts during reperfusion after hypothermic cardioplegic arrest according to Protocol 1. Open circle=Control hearts receiving no zinc. Closed circle=Test hearts receiving 30 μM zinc in the cardioplegic solution.
Figure 6B:
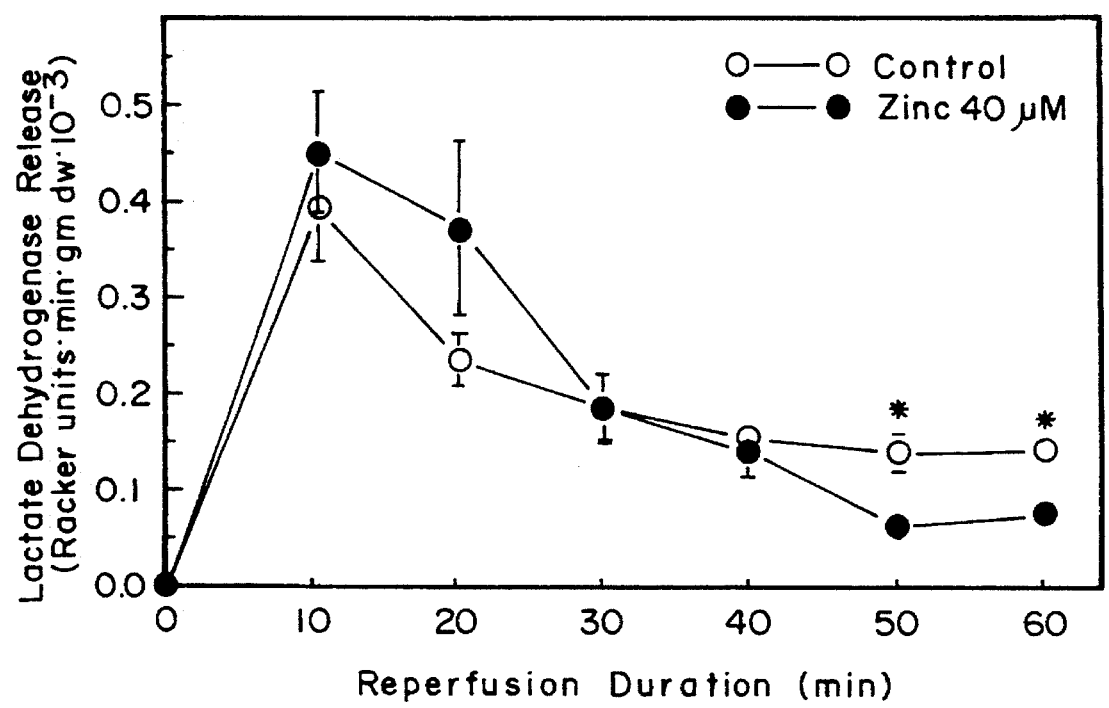
FIG. 6B depicts the amount of lactate dehydrogenase released from isolated rat hearts during reperfusion after hypothermic cardioplegic arrest according to Protocol 2. Open circle=Control hearts receiving no zinc. Closed circle=Test hearts receiving 40 μM zinc in the cardioplegic solution.

As illustrated in FIG. 6, zinc-treatment has virtually no effect on LDH release, except for a minor increase observed towards the end of reperfusion period for Protocol 2 treated hearts only.

The results of this study demonstrate that zinc supplementation of a standard cardioplegic solution, (e.g., St. Thomas No. 2) enhances the preservation of cardiac function after hypothermic arrest. Moreover the foregoing illustration can guide the skilled artisan in the selection of an administration regimen which is suited to the particular needs of each situation or patient. For example, prolonged perfusion with zinc-containing solutions was generally not necessary to obtain significant cardiac protection. Instead, to obtain optimal protection, the zinc-ligand conjugate can be administered at the onset of hypothermic arrest.

These observations therefore indicate that zinc conjugates have a clear clinical application during surgical procedures necessitating cardiopulmonary bypass, particularly at the initiation of cardioplegia, for preserving myocardial tissues.

What is claimed

1. In a method of improving recovery of a mammal after surgery when the heart of said mammal is subjected to cardioplegia by infusion with a cardioplegic solution at a hypothermic temperature; an improvement comprising infusing said heart for a sufficient time during at least the onset of cardioplegia with a cardioplegic solution which contains a sufficient amount of zinc complexed to a physiologically acceptable ligand, to improve cardiac function and recovery of the mammal after surgery.

2. The method of claim 1 wherein said sufficient amount of zinc is about 1.5 micromoles to about 150 micromoles.

3. The method of claim 1 wherein said infusion with cardioplegic solution is antegrade infusion.

4. The method of claim 1 wherein said infusion with cardioplegic solution is retrograde infusion.

5. A method of improving recovery of a mammal from surgery wherein the heart of said mammal is subjected to cardioplegia, which comprises infusing said heart for a sufficient time during at least the onset of cardioplegia with a cardioplegic solution which contains a sufficient amount of a zinc-ligand conjugate to deliver an effective dosage amount of zinc to myocardial tissue to improve cardiac function and recovery of the mammal after surgery.

6. A method of improving post-cardioplegic systolic pressure development in a heart of a mammal after surgery requiring cardioplegia, which comprises infusing said heart for a sufficient time during at least the onset of cardioplegia with a cardioplegic solution which contains a sufficient amount of a zinc-ligand conjugate to deliver an effective dosage amount of zinc to myocardial tissue to improve post-cardioplegic systolic pressure development.

7. A method of improving post-cardioplegic contractility in a heart of a mammal after surgery requiring cardioplegia, which comprises infusing said heart for a sufficient time during at least the onset of cardioplegia with a cardioplegic solution which contains a sufficient amount of a zinc-ligand conjugate to deliver an effective dosage amount of zinc to myocardial tissue to improve heart contractility.

8. A method of improving post-cardioplegic left ventricular relaxation in a heart of a mammal after surgery requiring cardioplegia, which comprises infusing said heart for a sufficient time during at least the onset of cardioplegia with a cardioplegic solution which contains a sufficient amount of a zinc-ligand conjugate to deliver an effective dosage amount of zinc to myocardial tissue to improve left ventricular relaxation.

9. The method of any one of claims 1–8 wherein said sufficient time is at least about 10 minutes to about 2 hours.

10. The method of any one of claims 1–8 wherein said cardioplegic solution is a crystalloid cardioplegic solution.

11. The method of any one of claims 1–8 wherein said cardioplegic solution is a crystalloid blood cardioplegic solution.

12. The method of any one of claims 1–8 wherein said ligand has a molecular weight of less than about 500 grams per mole.

13. The method of any one of claims 1–8 wherein said ligand is histidine, arginine, asparagine, lysine, proline, ethylenediamine, glycine, cysteine, aspartic acid or glutamic acid.

14. The method of any one of claims 1–8 wherein said ligand is an amino acid.

15. The method of claim 14 wherein said amino acid is histidine, arginine, asparagine, lysine or proline.

16. The method of any one of claims 5–8 wherein said hypothermic temperature is about 4° C. to about 10° C.

17. The method of any one of claims 1–8 wherein said hypothermic temperature is about 8° C.

18. The method of any one of claims 1–8 wherein said mammal is a human patient.

19. The method of any one of claims 5–8 wherein said sufficient amount of said conjugate is about 1.5 micromoles to about 150 micromoles.

20. The method of claim 1 wherein said zinc is administered at the same time as immediate diastolic arrest.

21. The method of any one of claims 5–8 wherein said zinc-ligand conjugate is administered within at least about 5 minutes of immediate diastolic arrest.

22. The method of any one of claims 5–8 wherein said zinc-ligand conjugate is administered at the same time as immediate diastolic arrest.

23. The method of any one of claims 5–8 wherein the zinc-ligand conjugate contains one part zinc and two parts histidine.

* * * * *

UNITED STATES PATENT AND TRADEMARK OFFICE
CERTIFICATE OF CORRECTION

PATENT NO. : 5,462,524
DATED : October 31, 1995
INVENTOR(S) : Saul R. Powell, et al.

It is certified that error appears in the above-indentified patent and that said Letters Patent is hereby corrected as shown below:

On the Title Page, item [56], Column 2, line 23: "pull and push" should read --"pull"-- and --"push"--

On the Title Page, Section [56], page 2, Column 2, line 8: "Bbiol." should read --Biol.--

Column 14, line 46, Claim 9: "1-8" should read -- 1 and 5-8--.

Column 14, line 48, Claim 10: "1-8" should read -- 1 and 5-8--.

Column 14, line 50, Claim 11: "1-8" should read -- 1 and 5-8--.

Column 14, line 53, Claim 12: "1-8" should read -- 1 and 5-8--.

Column 14, line 56, Claim 13: "1-8" should read -- 1 and 5-8--.

Column 14, line 60, Claim 14: "1-8" should read -- 1 and 5-8--.

UNITED STATES PATENT AND TRADEMARK OFFICE
CERTIFICATE OF CORRECTION

PATENT NO. : 5,462,524
DATED : October 31, 1995
INVENTOR(S) : Saul R. Powell, et al.

It is certified that error appears in the above-indentified patent and that said Letters Patent is hereby corrected as shown below:

Column 14, line 64, Claim 16:   "5-8"   should read
-- 1 and 5-8--.

Column 14, line 66, Claim 17:   "1-8"   should read
-- 1 and 5-8--.

Column 15, line 1, Claim 18:   "1-8"   should read
-- 1 and 5-8--.

Column 15, line 3, Claim 19:   "5-8"   should read
-- 1 and 5-8--.

Column 15, line 8, Claim 21:   "5-8"   should read
-- 1 and 5-8--.

Column 16, line 2, Claim 22:   "5-8"   should read
-- 1 and 5-8--.

Column 16, line 5, Claim 23:   "5-8"   should read
-- 1 and 5-8--.

Signed and Sealed this

Third Day of September, 1996

Attest:

BRUCE LEHMAN

*Attesting Officer*   *Commissioner of Patents and Trademarks*